US006848211B2

(12) United States Patent
Blanchette et al.

(10) Patent No.: US 6,848,211 B2
(45) Date of Patent: Feb. 1, 2005

(54) CULTIVATED AGARWOOD

(75) Inventors: Robert A. Blanchette, Shoreview, MN (US); Henry Heuveling van Beek, Amsterdam (NL)

(73) Assignee: Regents of the University of Minnesota, Minneapolis, MN (US)

( * ) Notice: Subject to any disclaimer, the term of this patent is extended or adjusted under 35 U.S.C. 154(b) by 319 days.

(21) Appl. No.: 09/863,381

(22) Filed: May 24, 2001

(65) Prior Publication Data

US 2002/0194780 A1 Dec. 26, 2002

(51) Int. Cl.$^7$ ................................. A61H 5/00
(52) U.S. Cl. ....................................... 47/58.1
(58) Field of Search ................................. 47/8

(56) References Cited

PUBLICATIONS

"Agarwood, Aloeswood and Oud—Jin–koh", http://www.oller.net/agarwood.htm, 5 p., (Oct. 2000).
Barden, A., et al., *Heart of the Matter: Agarwood Use and Trade and Cites Implementation for Aquilaria Malaccensis*, Traffic Network Report, 1–51, (1998–2000).
Blanchette, R.A., "Chapter 5: Anatomical Responses of Xylem to Injury and Invasion by Fungi", *In: Defense Mechanisms of Woody Plants Against Fungi*, Springer–Verlag, R.A. Blanchette, et al., (Eds.), pp. 76–95, (1992).
Bose, S.R., "The Nature of "Agaru" Formation", *Science & Culture, IV* (3), pp. 89–91, (Aug. 1938).
Burkill, I.H., et al., *A Dictionary of the Economic Products of the Malay Peninsula, 1*, Crown Agents for the Colonies, London, pp. 197–205, (1935).
Gibson, I., "The Role of Fungi in the Origin of Oleoresin Deposits (Agaru) in the wood of Aquilaria Agallocha Roxb", *Bano Biggyan Patrika, 6* (1), pp. 16–26 (Jan. 1977).
Hansen, E., "The Hidden History of a Scented Wood", *Saudi Aramco World, 51* (6), pp. 1–13, (Nov./Dec. 2000).
Ishihara, M., et al., "Preparation of (–)–Guaia–1(10), 11–dien–15, 2–olide and (–)–2alpha–Hydroxyguaia–1(10), 11–dien–15–oic Acid, Fragrant Sesquiterpenes in Agarwood (*Aquilaria agallocha* Roxb.)", *Tetrahedron Letters, 48* (47), pp. 10265–10276, (1992).

Ishihara, M., et al., "Three Sesquiterpenes From Agarwood", *Phytochemistry, 30* (2), pp. 563–566, (1991).
Punithalingam, E., et al., "Phomopsis Species From *Aquilaria Agallocha*", *Nova Hedwigia, 29*, pp. 251–255, (1978).
Ng, L.T., et al., "A Review of Agar (Gaharu) Producing Aquilaria Species", *Journal of Tropical Forest Products, 2* (2), (1997), pp. 272–285.
Siemonsma, J.S., et al., *Plant Resources of South East Asia*, Proceedings of the first PROSEA Int'l Symposium, Jakarta, Indonesia, (1989), 13 pp.
Rahman, M.A. & Basak, A.C. *Agar Production in Agar Tree By Artificial Inoculation & Wounding* pp. 87–92, 1980.*
Blanchette, R.A. & Biggs, A.R. *Defense Mechanisms of Woody Plants Against Fungi* pp. 79–92, 1992.*
Gibson, I.A.S. *The Role of Fungi in the Origin of Oleoresin Deposits (Agaru) in the Wood of Aquilaria Agallocha Roxb.* pp. 17–20, 1977.*
Rahman, M.A., et al., "Agar Production in Agar Tree By Artificial Inoculation and WOunding", *Bano Biggyan Patrika, 9* (*1* & *2*), pp. 87–93, (1980).
Rao, K.R., et al., "The Secondary Xylem of Aquilaria Agallocha (Thymelaeaceae) and the Formation of 'Agar'", *International Association of Wood Anatomist Bulletin (IAWA), N.S., 13* (2), pp. 163–172, (1992).
Schuitemaker, J.P., "Garoe Wood From West Borneo", *Boschbouwkundig Tijdschrift Tectona Uitgave der Vereeniging van Hoogere Ambtenaren bij het Boschwezen in Nederlands Oost–Indi, 26*, Translated from Dutch by the Ralph McElroy Translation Company, 910 West Avenue, Austin, Texas 78701, pp. 851–892, (1933).
Yoneda, K., et al., "Sesquiterpenoids in Two Different Kinds of Agarwood", *Phytochemistry, 23* (9), pp. 2068–2069, (1984).
Paoli, Gary D., et al., "An Ecological and Economic Assessment of the Nontimber Forest Product Gaharu Wood In Gunung Palung National Park, West Kalimantan, Indonesia", *Conservation Biology, vol. 15, No. 6*, (Dec. /2001), 1721–1732.

* cited by examiner

*Primary Examiner*—Bruce R. Campbell
*Assistant Examiner*—Michelle Kizilkaya
(74) *Attorney, Agent, or Firm*—Fish & Richardson P.C., P.A.

(57) ABSTRACT

The present invention provides agarwood from cultivated trees, and methods of generating agarwood in cultivated trees.

41 Claims, 5 Drawing Sheets

CULTIVATED AGARWOOD

BACKGROUND OF THE INVENTION

Agarwood is a highly prized incense that is extremely rare. It has at least a 3000-year history in the Middle East, China and Japan. There are also references to agarwood in the literature of India and France, and even in the Old Testament of the Bible. Agarwood remains today the world's most expensive incense. The value of agarwood shipped out of Singapore alone each year has been estimated to exceed $1.2 billion. E. Hansen, *Saudi Aramco World* 51:2–13 (December 2000). This aromatic resinous wood has many common names including agarwood, gaharu, eaglewood, aloeswood, agila wood, aguru, agar, oud, ude, ud, ood, oode, jinkoh, jinko, Ch'Ing Kuei Hsiang, Ch'En Hsiang, Chan Hsiang, Chi Ku Hsiang, Huang Shu Hsiang, kalambak, and grindsanah.

The resin is used by Traditional Chinese, Unanai, Ayuravedic, and Tibetan physicians. Used medicinally, agarwood is a remedy for nervous disorders such as neurosis, obsessive behavior, and exhaustion. Agarwood is highly psychoactive and is used in spiritual rituals. Many religious groups prize it as a meditation incense, to calm the mind and spirit. In Ayuravedic medicine it is used to treat a wide range of mental illness and to drive evil spirits away. In Japan, it is considered by many to be sacred, and is used to anoint the dead. In Buddhism, it serves as a major ingredient in many incense mixtures, and it is considered to be one of the three integral incenses, together with sandalwood and cloves.

The source of agarwood is the Aquilaria tree. The Aquilaria tree is an evergreen that grows up to 40 meters high and 60 centimeters in diameter. It bears white flowers that are sweetly scented. The genus Aquilaria is an angiosperm taxonomically placed in the Thymelaceaceae family. Fifteen species of Aquilaria have been reported and all produce agarwood. The taxonomy of these species is not completely clear and not all species are recognized by taxonomists. Species include *Aquilaria malaccensis, A. agallocha, A. baillonii, A. crassna, A. hirta, A. rostrata, A. beccariana, A. cummingiana, A. filaria, A. khasiana, A. microcarpa, A. grandiflora, A. chinesis* or *A. sinensis, A. borneensis,* and *A. bancana. Aquilaria bancana* has been questioned as a true species of Aquilaria and has been placed in the Gonystylaceae family of the Gonystylus genus, as *Gonystylus bancanus.* Gonystylus has also been found to produce an aromatic resin that is considered the same as or very similar to agarwood.

Aquilaria trees are native to Asia from Northern India to Vietnam and Indonesia. The healthy wood of the Aquilaria tree is white, soft, even-grained, and not scented when freshly cut. Under certain pathological conditions, the heartwood becomes saturated with resin, and eventually becomes hard to very hard. The best grade of agarwood is hard, nearly black and sinks when placed in water. In general, agarwood is considered inferior as it appears lighter in tone, with diminishing amounts of resin.

The process of agar deposits is not fully understood. A Dutch paper from 1933 (J. P. Schuitemaker, "Het garoehout van West Boreno" Boschbouwkundig Tijdschrift Tectona Uitgave der Vereeniging van Hoogere Ambtenaren bij het Boschwezen in Nederlands Oost-Indi 26:851–892) reported the occurrence of agarwood in Borneo and discussed many different types of resin produced in trees. Most of the local people at the time believed that agarwood formed from mysterious ways and was associated with the spirit world. The author stated that "the mysterious occurrence of the 'holy' wood is connected to supernatural powers" and that agarwood was referred to as "wood of the gods." The author also noted that "we cannot exclude the possibility of a pathological occurrence of which the cause was unknown," that "perfect trees never have agarwood," and that agarwood "is formed around wounded or rotting parts of the trunk." The author also suggested that salt put into holes in trees might promote resin. The paper also stated that if the agarwood was infectious, maybe it would be possible to induce agarwood formation by infecting the trunk artificially by putting fresh cut agarwood into the stem.

Later authors also reported the longstanding belief was that agar deposits were created as an immune response by the tree, the result of attack by a fungus. I. H. Burkill, *A dictionary of the economic products of the Malay Peninsula. Vol. I Crown Agents for the Colonies,* London p. 197–205. In the 1940's and 1950's, several researchers investigated the origins of agar deposits with varying and sometimes conflicting results. Rahman and Basak, *Bano Biggyan Patrika* 9:87–93 (1980). Others concluded that it was unlikely that there was a specific fungal cause for the production of agarwood. Gibson, *Bano Biggyan Patrika* 6:16–26 (1977). It was suggested that the resin deposits might arise as a direct response of the stem tissues of the tree to wounds with subsequent invasion by weak pathogens. Id.

Rahman and Basak suggested that wounding produced color changes in the wood with some "oleoresin" deposits. Rahman and Basak, *Bano Biggyan Patrika* 9:87–93 (1980). They postulated that the presence of an exposed, open wound seemed to be of more importance than the presence of certain species of fungi within a wound. They, however, concluded their paper by stating that further investigation was needed in order to determine what factors were responsible in wounding, which are important in agar deposition.

The identification of the small proportion of the trees having agar is difficult and destructive, which added greatly to the near-extinction of natural stands of tress. Also, large-scale logging operations have destroyed many forested areas where the Aquilaria trees are found. Thus, the current source of agarwood, the naturally-growing old-growth Aquilaria trees, is becoming extinct. To date no one has successfully cultivated agarwood. E. Hansen, *Saudi Aramco World* 51:2–13 (December, 2000). Therefore, there is a growing need for a means to cultivate Aquilaria trees that produce agarwood as a renewable source for agarwood.

SUMMARY OF THE INVENTION

The present invention provides a method of producing agarwood by forming an artificial wound into the xylem in an Aquilaria or Gonystylus tree, and providing a means for aerating the wound. Additional wounds may be formed either at the same time or after a discolored area has begun forming in the tree. The wound may be formed by cutting, drilling, or chopping or by inserting a nail. The wound is formed to reach the xylem. The wound may be formed to a depth of at least about 1 to 10 cm into the xylem. In one embodiment the wound is formed to a depth of about 4–6 cm. The wounds may be made as a series of closely spaced wounds in the tree. For example, the series of wounds, such as about 30–100 wounds, may be positioned in a spiral up the tree. The wounds may be positioned at an interval of about 5 cm apart.

In the present method, the aeration means may be an aeration device inserted into the wound, such as a nail, tube or pipe inserted into the wound. The aeration device may contain aeration holes in it and/or it may contain grooves on its exterior surface. The aeration device may be made of plastic, bamboo, wood or other organic material, or metal, such as iron. It may be about 2 cm in diameter. When inserted, the aeration device may extend out from the exterior of the tree, such as about 2 to 15 cm from the exterior of the tree.

Alternatively, the aeration means of the present invention may be a periodic (e.g., monthly) re-wounding of the wound. This may be by scribing a patch of cambium around the wound one or more times over the life span of the tree. It may also be by removing a region of cambium adjoining the wound.

The present method may also involve applying a resin-inducing agent to cells surrounding the wound. This resin-inducing agent stimulates resin production in the tree. It may kill live parenchyma cells around the wounded region of the xylem. The resin-inducing agent may be a chemical agent. If a chemical agent is used, it may kill cells locally. It can be, for example, sodium bisulfite, NaCl, ferric chloride, ferrous chloride, chitin, formic acid, cellobiose, salicyclic acid, iron powder, or yeast extract. In particular, it may be 1:1:3 sodium bisulfite, Difco yeast extract and iron powder. Alternatively, or additionally, the resin-inducing agent may be an organism, such as an insect or microbe, such as a fungus (e.g., *Deuteromyota* sp., *Ascomycota* sp., *Basidiomycota* sp.)

The tree that is used in the present invention is less than 100 years old, preferably is about 2–80 years old, more preferably 3–20 years old, or even only about 3–12 years old. The tree used in the present invention is not growing naturally in an old growth forest. An "old growth forest" is defined herein as a forest that is ecologically mature and has been subjected to negligible unnatural disturbance such as logging, roading and clearing. Also included in this definition are ecologically mature forests where the effects of disturbance are now negligible. In such old growth forests, the upper stratum or overstory is in the late mature to over-mature growth phases. Species of trees that can be used in the present invention include, for example, *Aquilaria malaccensis, A. agallocha, A. baillonii, A. crassna, A. hirta, A. rostrata, A. beccariana, A. cummingiana, A. filaria, A. khasiana, A. microcarpa, A. grandiflora, A. chinesis* or *A. sinensis, A. borneensis,* and *A. bancana,* or *Gonystylus bancanus.*

The present invention also provides agarwood produced by the methods described above. The present invention further provides agarwood from a tree grown in a home garden, in a plantation, in a greenhouse, or in agricultural lands.

It should be noted that the indefinite articles "a" and "an" and the definite article "the" are used in the present application, as is common in patent applications, to mean one or more unless the context clearly dictates otherwise.

DETAILED DESCRIPTION OF THE INVENTION

Aquilaria has a unique anatomy, and one who wishes to induce agarwood in young trees must understand its anatomy. Unlike most trees in the Angiospemae that produce phloem cells external to the xylem (growing out from the circumference of the cambium), Aquilaria produces bundles of phloem cells throughout the xylem as well as in a layer external to the xylem. This means that the xylem (consisting of vessels, fibers and parenchyma cells) also contains groups of phloem cells called included phloem or interxlyary phloem of the diffuse (foraminate) type. When trees are wounded they respond by forming new wood cells by the cambium. These cells differentiate and close the wound with newly produced cells (Blanchette R. A. 1992. *Anatomical responses of xylem to injury and invasion by fungi. In: Defense Mechanisms of Woody Plants Against Fungi.* Edited by R. A. Blanchette and A. R. Biggs. Springer-Verlag Berlin. Pp. 76–95). Once the wound is closed, aeration to the affected wood stops and internal processes needing air cease. Most trees close wounds by producing new cells at the edge of the wounded cambium. Aquilaria trees close wound from inside the xylem as well as externally.

Figure 1:
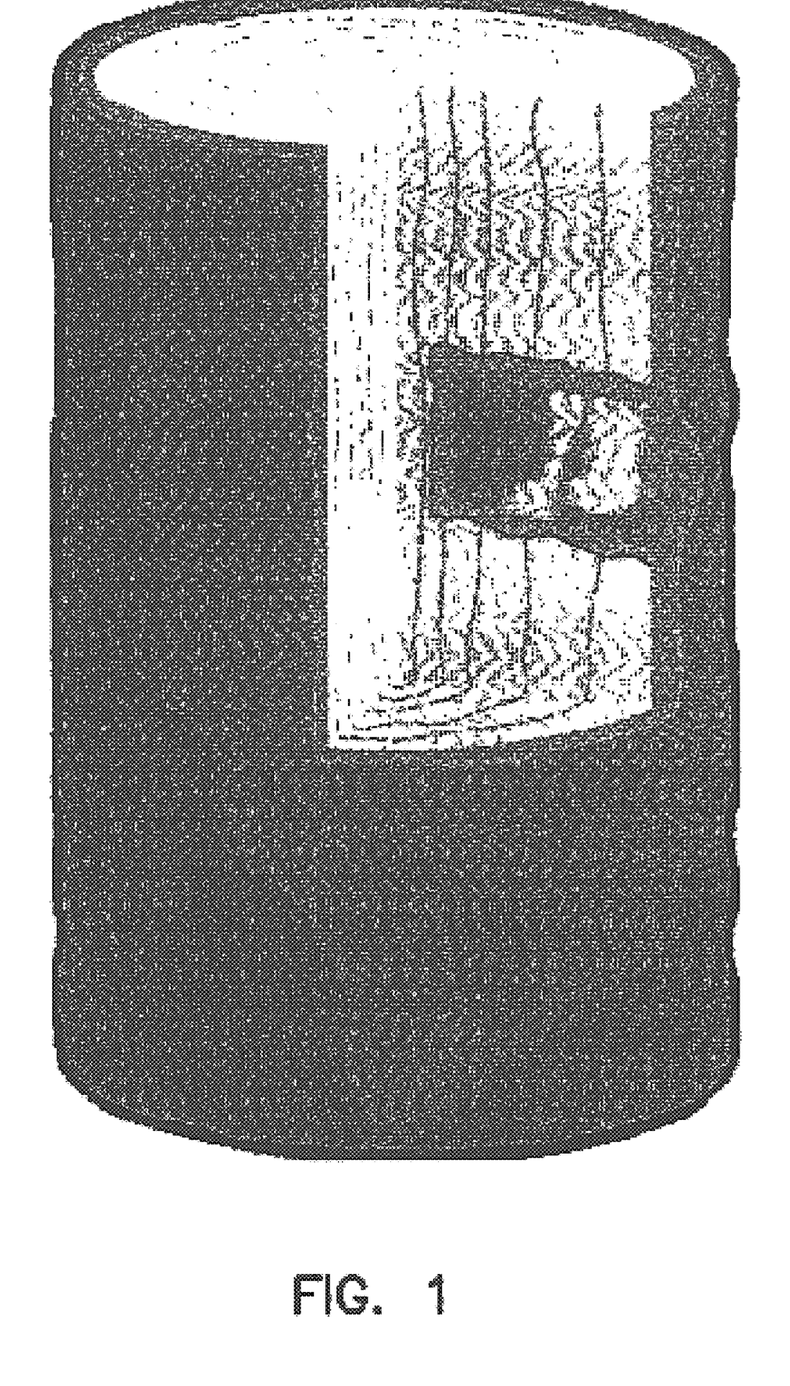
FIG. 1. Schematic drawing of wounded Aquilaria tree at time of harvest with nothing done to promote agarwood showing internal callus formation produced by bundles of included phloem cells, and wound closure from inside the drill wound. Surface cells also produce callus tissue and wound closure occurs from the outer edge of the drill wound. Little discoloration forms and insignificant amounts (if any) of agarwood may form in a very thin band between the discolored wood and the sound, unaltered xylem.

The present experiments have shown that the cambium of Aquilaria trees reacts to wounding by producing new cells all around the wound and even on the surface of the wound. See FIG. 1. Phloem cells apparently produce new cambial cells that produce new differentiated wood cells. Wound closure occurs rapidly. Phloem bundles on the surface of the exposed xylem produce secondary cambial cells that produce new cells to seal and close the wound. Large surface wounds do not close by only producing callus at the edge of the wounds (like most trees) instead the entire surface of the exposed xylem produces new cambial cells which in turn differentiate producing new wood cells that close the wound.

Although wounding has been suggested to cause agarwood, the typical types of wounds that are produced in trees produce no agarwood. If artificial wounds are made into the xylem by boring into the tree, the included phloem present throughout the wounded site reacts and may produce new cambial cells. New wood formed from this new cambium will grow within the wounded xylem. This seals and closes the internal wound. Aquilaria trees with internal wounds can seal and close wounds from the inside of the trees as well as along the wounded surface of the exterior surfaces of the tree. The present experiments show that wound closure stops agarwood formation.

The literature has suggested that fungi growing in the wounded Aquilaria tree may cause agarwood formation. Different types of fungi have been suggested including *Phialophora parasitica, Torula* sp., *Aspergillus* sp., *Penicil-* lium sp., *Fusarium* sp., *Cladosporium* sp., *Epicoccum granulatum, Cylimndrocladium, Sphaeropsis* sp., *Botryodiplodia theobromae, Trichoderma* sp., *Phomopsis* sp., and *Cunninghamella echinulata*. With all of these fungi suggested as a possible cause and no clear definitive research to show that a fungus is responsible for agarwood to form, researchers have indicated "that agaru arises from a much more generalized cause than previously invisaged" (Gibson, *Bano Biggyan Patrika* 6:16–26 (1977)). Punithalingam and Gibson, *Nova Hedwigia* 29:251–255 (1978) report a new species of *Phomopsis* from Aquilaria but indicate "no evidence was obtained to show that this fungus was the cause of the formation of agaru." In a paper by Rahman and Basak (*Bano Biggyan Patrika* 9:87–93 (1980)) on "Agarwood production in agar tree by artificial inoculation and wounding" after experiments to produce agarwood they concluded, "More experimental work needs to be done before the generation of agar deposit is fully understood. There is no doubt that we are still far from the development of techniques which would provide an assured supply of agar products." The paper by Rao and Dayal (*International Association of Wood Anatomist Bulletin N.S.*, 13:163–172 (1992)) discusses the formation of agarwood and provides microscopic views of affected wood from naturally growing trees with agarwood. They conclude by suggesting that "it is important to study factors such as tree age, within-tree seasonal variation in responsiveness, and environmental variation" to determine how agarwood is formed. Research by the present inventors has shown that tree age is not important (planted young trees not growing naturally in a forest can produce agarwood) and agarwood has been produced in trees at three different geographical locations in Vietnam showing variation in the environment is not a critical factor.

Agarwood is a resinous wood substance that is produced by the tree as a nonspecific host response to wounding, insects and/or microbial invasion. The resin contains tree extractives that have aromatic terpenes present. As discussed above, Aquilaria is unique in that it produces phloem bundles within the xylem. This network of phloem and parenchyma cells produce and distribute the resin around affected areas as a tree defense reaction. It was previously thought that only old trees could produce resin.

The present inventors have determined how agarwood forms in nature and have used this information to produce agarwood in young cultivated Aquilaria trees. The trees may be grown, for example, in a home or cooperative garden, on a plantation, or in a greenhouse. The present technique for producing agarwood has been used on young plantation-grown trees, about 3 to 8 years old. The technique can be performed on trees that are older than this, although for economic reasons, it is beneficial to use younger trees. The inventors have found that two factors are needed in order to induce the production of agarwood in Aquilaria trees: (1) an open wound in the tree, and (2) this open wound must be aerated.

Figure 2A:
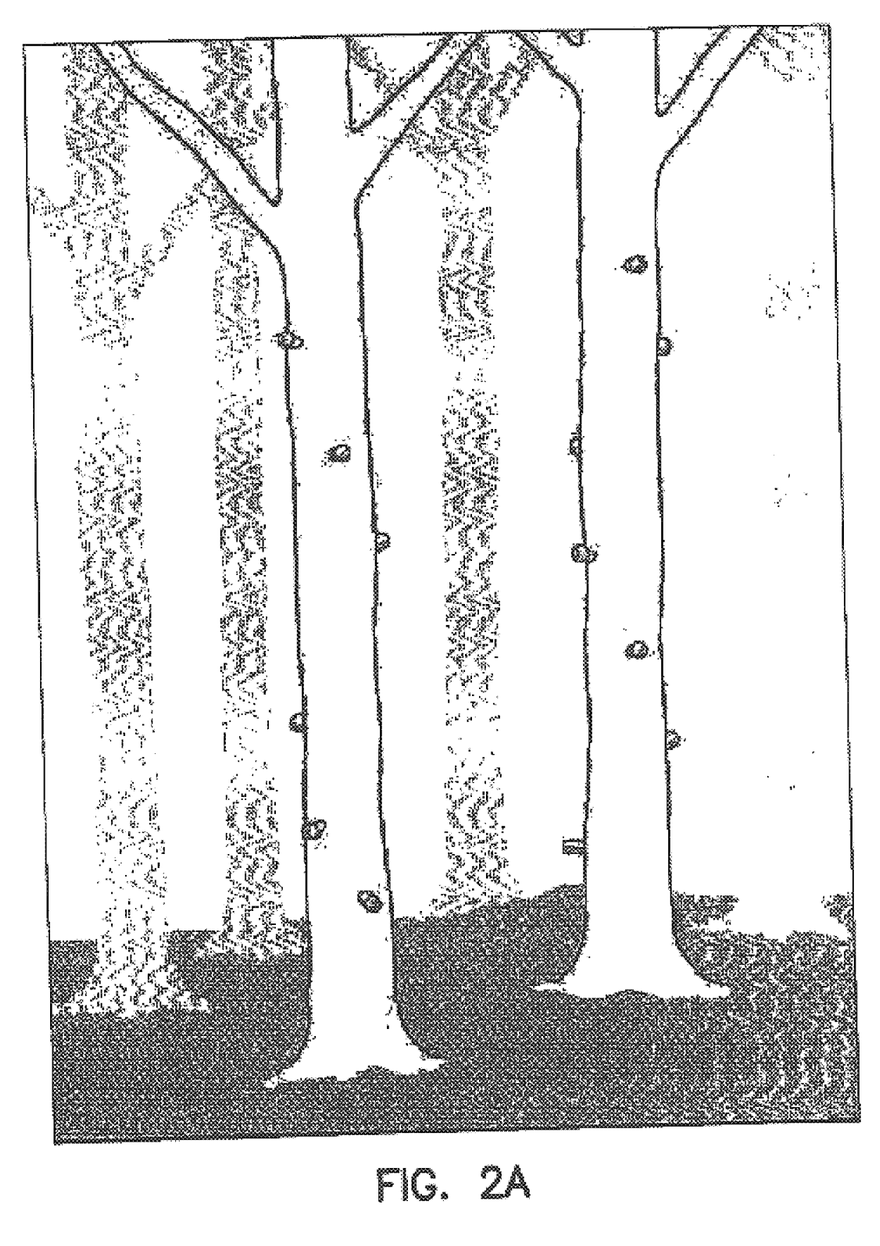
FIG. 2A. Schematic drawing of Aquilaria tree that was wounded and tube with aeration holes inserted.
Figure 2B:
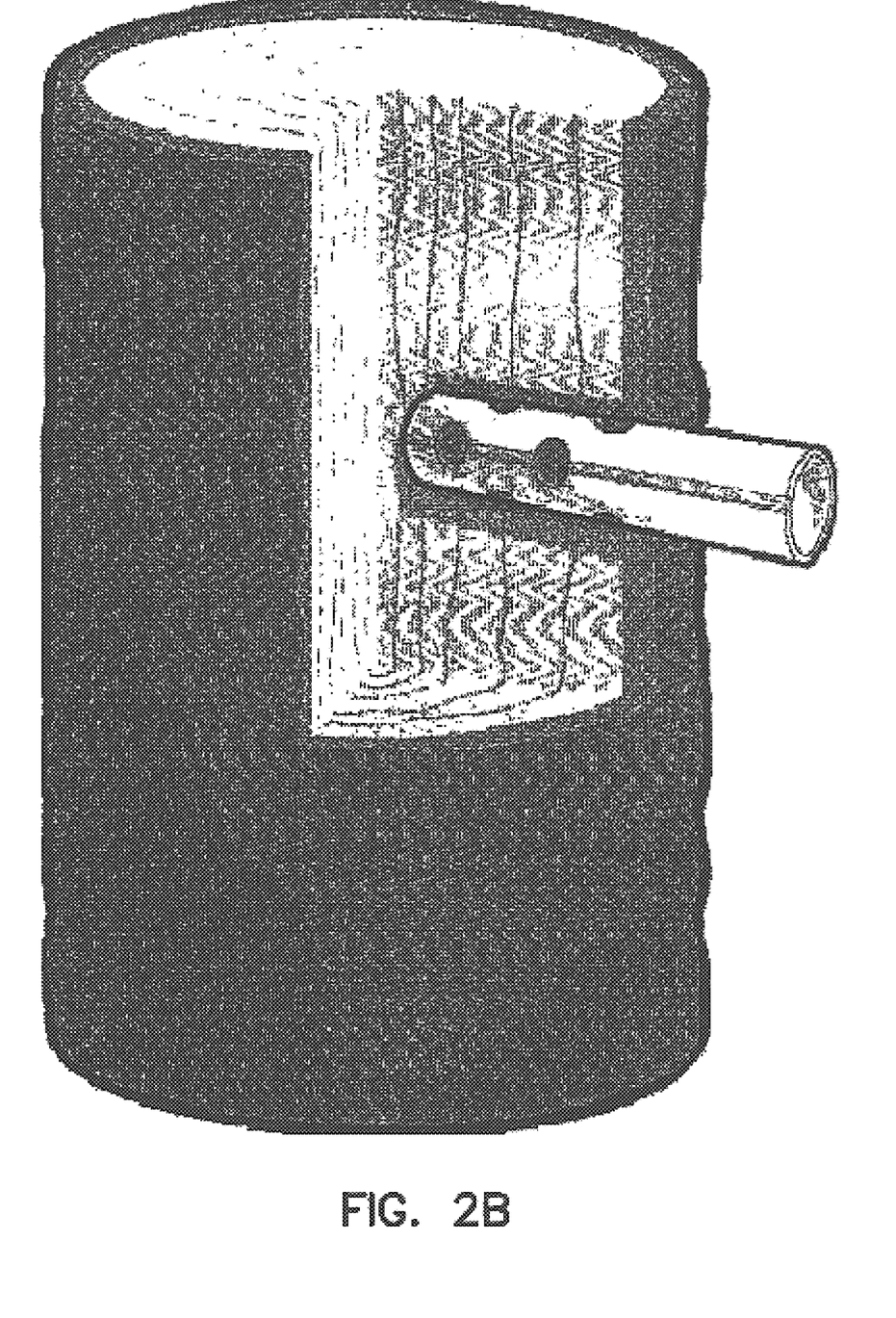
FIG. 2B. Drawing of trees that were wounded and had multiple aeration tubes inserted into the trees.

Trees are wounded with a drill to make a hole into the xylem. Many types of wounds were tried and a hole that cuts across the xylem is needed. The size of the hole is not important. Of prime importance is that the hole must not be closed by callus tissue. Small drill wounds may close by new wood growth within one year in fast-growing tropical trees. To insure that the wound does not close, a region of cambium can be cut around the drill wound. This removes the cambium and delays callus formation and wound closure. This process needs to be done repeatedly if the wound appears to be closing. Another method is to insert a sturdy plastic, bamboo, wood or other organic material, or metal tube or pipe (with holes made all along the sides of the tube) into the drill wound leaving it protruding out of the tree. See FIGS. 2A and 2B. As the tree grows, the tube prevents the tree from closing the wound. These and any other methods to prevent wound closure can be used.

Figure 3:
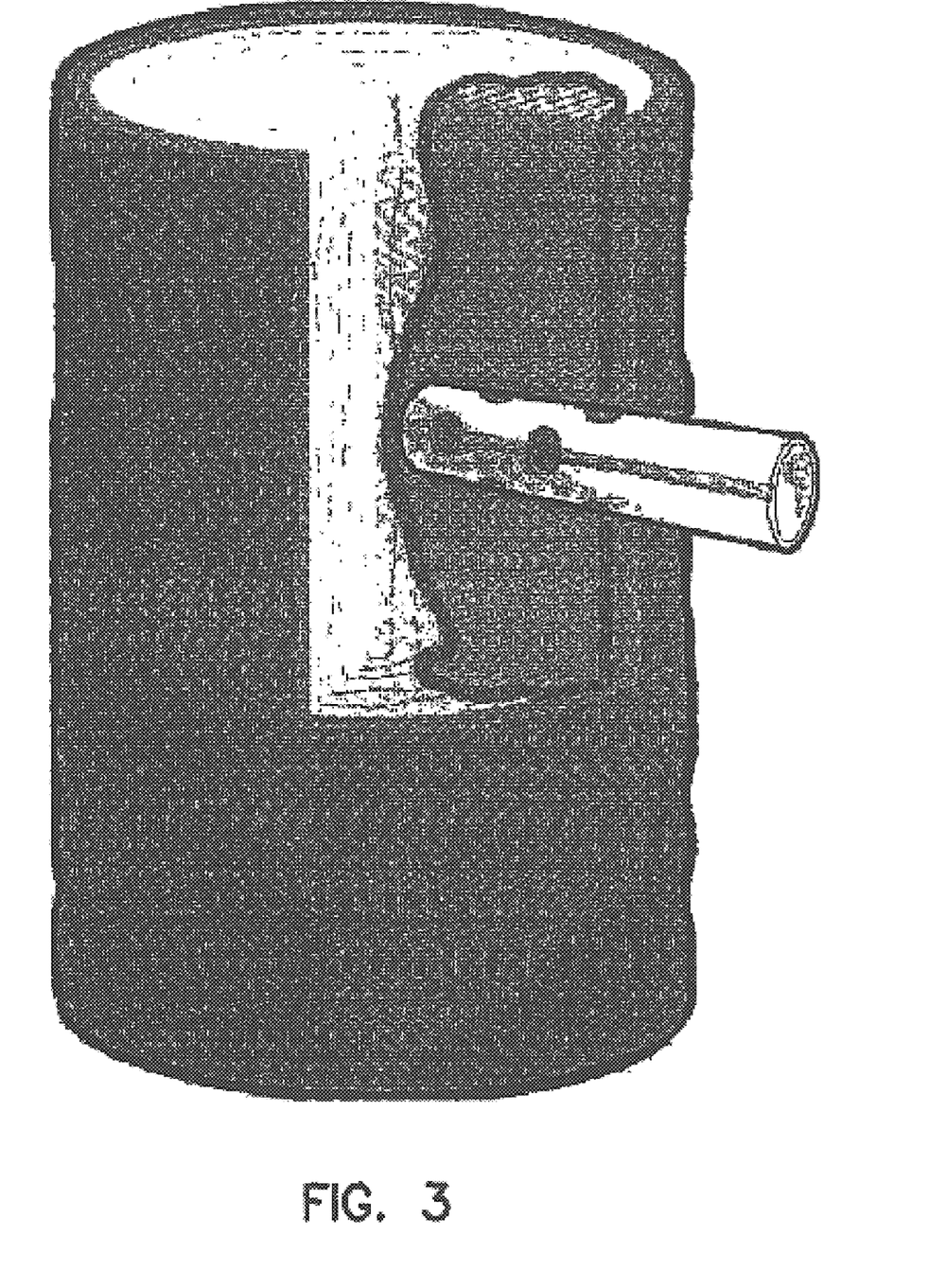
FIG. 3. Schematic drawing showing wounded Aquilaria tree at time of harvest with plastic tube inserted into the drill hole. Tree was treated with sodium bisulfite. A discolored region around the wounded area extends above, below and around the wound. An area of agarwood resin forms in a thick band between the discolored wood and the sound, unaltered xylem. This area of agarwood production gets larger and more dense over time.

In order to maximize agarwood production, one can disturb the tree cells that line the hole after the hole is made. It was seen that the more disruption of live cells, the greater the internal area where agarwood formed. If a hole is drilled, agarwood forms only around the edge of the wound (and only while aeration occurs). If a drill wound is made and substances that kill some of the tree cells (resin-inducing agents) are introduced, the resin forms over a much larger area. See FIG. 3. Many different resin-inducing substances can be used, such as NaCl, ferric chloride, ferrous chloride, chitin, formic acid, etc. Also microbes can be inoculated into the tree to induce a more intense host response. Species of fungi, taxonomically from the Deuteromycota, Ascomycota and Basidiomycota groups that were isolated from agarwood columns in old growth trees growing in Viet Nam were inoculated into the test trees. The presence of some fungi may help keep the wound open and disrupt live cells of the tree, therefore acting as an inducing agent. The sesquiterpenes produced in agarwood from naturally occurring resin in old growth trees and in young plantation-grown trees were chemically analyzed, and the resin was the same.

In one embodiment of the invention, the method would include a series of drill wounds made in a spiral up the tree (30 to 100+ per tree). Each wound is separated by a short interval. Each wound receives a tube, such as a plastic tube, with many holes in its walls. The tube is inserted into the drill wound and left to extend out from the tree 2 to 15 cm. The tube would also contain an inducing agent.

Another method would be to drill holes that are spiraled up the tree and the inducing agent is added directly into the wounds. Each wound would be scribed to cut away a patch of cambium around the hole. The wounds would be inspected over time and new scribing and/or drilling used to keep the hole open. Trees may be grown in nature or in greenhouses for agarwood production.

The following examples are intended to illustrate but not limit the invention.

EXAMPLES

Trees, approximately 4–5 years old, growing in plantations in An Giang Province or Phu Quoc Island, Vietnam were used for experiments 1 to 8.

Example 1

Trees were wounded by making six ax wounds into the main trunk on each tree. Trees harvested after six months were cut and split through the wounded area. The area of discoloration was measured on the exposed longitudinal plane. Resin formation (agarwood) occurred (if it occurred) in a small zone between the wounded, discolored wood and the live unaltered wood. After 6 months, the mean area of discoloration of six ax wounds was 6.1 cm$^2$ ranging from 1.6 to 9.1 cm$^2$ and no distinct area of resin formation was seen. After 21 months, the mean area of six ax wounds was 0.3 cm$^2$ ranging from 0.0 to 1.5 cm$^2$ and no resin was apparent. The results from this study show that wounding trees with an ax and making shallow surface wounds does not produce agarwood.

Example 2

Trees were wounded with a ⅝ inch drill to a depth of approximated 5 cm. Six wounds were made in a spiral fashion on the trunk of the tree approximately 20 cm apart. One of the six wounds served as a control and the other 5 wounds were filled with agarwood (approximately 0.5 g per wound) from a tree in the forest with naturally produced agarwood. This tree had been cut by poachers but some parts of the tree remained and some fresh agarwood was obtained from it. Small sections of the agarwood were cut and put into the drill wounds. After 6 and 18 months trees were harvested and evaluated with the following results.

| Wound | Treatment | Area of discoloration |
|---|---|---|
| After 6 months | | |
| 1 | Control | 11.7 |
| 2 | agarwood | 27.6 |
| 3 | agarwood | 22.1 |
| 4 | agarwood | 15.6 |
| 5 | agarwood | 12.6 |
| 6 | agarwood | 16.0 |
| After 18 months | | |
| 1 | Control | 18.4 |
| 2 | agarwood | 16.9 |
| 3 | agarwood | 18.8 |
| 4 | agarwood | 19.1 |
| 5 | agarwood | 15.1 |
| 6 | agarwood | 17.6 |

The amount of discoloration was somewhat greater than when ax wounds were used and a very small region of what appeared to be resin was found at the interface between discolored wood and sound wood. However, trees rapidly closed and the agarwood formation process did not progress as seen in the relatively small areas of discoloration present after 18 months.

Example 3

Trees were wounded with a ⅝ inch drill to a depth of approximated 5 cm. Six wounds were made in a spiral fashion on the trunk of the tree approximately 20 cm apart. One of the six wounds served as a control and the other 5 wounds were inoculated with pure cultures of fungi isolated from fresh agarwood obtained from natural forests in Vietnam. Five different fungi, representing different species of Ascomyota and Deuteromycota, were used. The genus and species was not determined but culture morphology indicated each fungus represented different genera. Only cultures proving to be successful for stimulating agarwood were to be identified to species after field data was obtained. Fungi were grown on sterile oats supplemented with malt extract broth for added nutrients. Cultures were grown for 3 weeks on the oat/malt extract substrate. Drill wounds inoculated with the fungi were filled with the fungus/oat inoculum. After 6, 18 and 21 months the trees were harvested and the following results were obtained.

| Wound | Treatment | Area of discoloration |
|---|---|---|
| After 6 months | | |
| 1 | Control untreated | 24.8 |
| 2 | Isolate F-4 | 20.2 |
| 3 | Isolate F-5 | 17.7 |
| 4 | Isolate F-9 | 14.6 |
| 5 | Isolate F-24 | 15.6 |
| 6 | Isolate F-32 | 11.7 |
| After 18 months | | |
| 1 | Control untreated | 8.8 |
| 2 | Isolate F-4 | 7.7 |
| 3 | Isolate F-5 | 12.5 |
| 4 | Isolate F-9 | 8.6 |
| 5 | Isolate F-24 | 1.6 |
| 6 | Isolate F-32 | 13.3 |
| After 21 months | | |
| 1 | Control untreated | 10.2 |
| 2 | Isolate F-4 | 8.6 |
| 3 | Isolate F-5 | 11.4 |
| 4 | Isolate F-9 | 10.8 |
| 5 | Isolate F-24 | 9.9 |
| 6 | Isolate F-32 | 11.7 |

The results indicate that the common fungi associated with fresh agarwood in Vietnam did not significantly stimulate agarwood to form. The area of discoloration and intermediate area of very slight amounts of resin production was similar between the non-inoculated drill wounds and wounds receiving pure cultures of fungi. No significant increases in agarwood production occurred over the three harvest dates.

Example 4

Trees were wounded with a ⅝ inch drill to a depth of approximated 5 cm. Six wounds were made in a spiral fashion on the trunk of each tree approximately 20 cm apart. Two of the six wounds served as controls and the other 4 wounds were inoculated with different types of nutrient growth media (used to culture microorganisms in the laboratory) or soil.

Treatments included:

Control no treatment

Difco Malt Extract (ME) approximately 0.1 g added per wound

Difco mycological agar (MYCO) approximately 0.1 g added per wound

Difco yeast extract (YE) approximately 0.1 g added per wound

Soil approximately 0.25 grams of soil from the plantation where the tree was growing was added per wound

| Wound | Treatment | Area of discoloration |
|---|---|---|
| After 12 months | | |
| 1 | Control no treatment | 16.7 |
| 2 | ME | 11.2 |
| 3 | MYCO | 12.3 |
| 4 | YE | 8.1 |
| 5 | Soil | 7.3 |
| 6 | Control no treatment | 6.4 |
| After 21 months | | |
| 1 | Control no treatment | 6.0 |
| 2 | ME | 7.2 |
| 3 | MYCO | 16.8 |
| 4 | YE | 10.8 |
| 5 | Soil | 10.5 |
| 6 | Control no treatment | 12.6 |

These results indicate that no inducement of agarwood was found when just nutrients used to grow fungi in culture were used. Soil placed into the drill wound also did not stimulate agarwood formation. All wounds had evidence of wound closure from surface cambium cells and the included phloem cells of the xylem produced new cells to close the wounds from within the drill hole.

Example 5

To test if different types of compounds could stimulate agarwood production, ⅝ inch drill wounds were made approximately 5 cm into the main trunk of young plantation trees and different materials used to treat the drill wounds. Chemicals used were from Sigma Chemicals Inc. St. Louis, Mo. or Mallinckrodt Inc. Paris, Ky. One drill wound per tree received no treatment and others received one of the following treatments:

Chitosan—purified chitin approximately 0.2 g of chitin was added per wound

Formic acid—approximately 0.1 g of formic acid was added per wound

Sodium chloride—approximately 0.2 g added per wound

Cellobiose—approximately 0.2 grams added per wound

Lime—approximately 0.1 g calcium carbonate added per wound

Trees were harvested after 12, 18 and 21 months.

| Wound | Treatment | Area of discoloration |
|---|---|---|
| After 12 months | | |
| 1 | Control no treatment | 11.2 |
| 2 | Chitosan | 9.0 |
| 3 | Formic acid | 28.5 |
| 4 | NaCl | 49.3 |
| 5 | Lime | 10.0 |
| 6 | Cellobiose | 9.9 |
| After 18 months | | |
| 1 | Control no treatment | 25.4 |
| 2 | Chitosan | 22.1 |
| 3 | Formic acid | 18.6 |
| 4 | NaCl | 44.7 |
| 5 | Lime | 18.7 |
| 6 | Cellobiose | 20.3 |
| After 21 months | | |
| 1 | Control no treatment | 11.1 |
| 2 | Chitosan | 3.8 |
| 3 | Formic acid | 31.8 |
| 4 | NaCl | 36.4 |
| 5 | Lime | 9.7 |
| 6 | Cellobiose | 7.4 |

These results indicate that the reaction area within a tree and area of discoloration can be increased with compounds that kill live parenchyma cells around the wounded region of the xylem. Deposits of agarwood resin were formed at the edges of the discolored regions. Substances like formic acid that have a low pH and NaCl that has a high pH both can disrupt live cells and induce greater amounts of agarwood than the control wounds. As the tree grows and wounds are closed the affected area decreases. Other substances like chitosan, cellobiose and lime do not increase the area of discoloration within the tree at the concentrations tested. However, if added at amounts that are detrimental to live cells adjacent to the wounded area it did have an effect. Microscopic observations indicate that the cells around wounds treated with NaCl or formic acid react extensively and phloem cells are filled with resin. These cells do not have the ability to produce cambial initial cells and wound closure is delayed. Substances that affect the live parenchyma cells and phloem cells in the xylem stimulate resin production and induce agarwood production. They also inhibit wound closure from the outer cambium as well as new cells formed by the included phloem.

Example 6

Analysis of the chemical composition of natural agarwood and experimentally produced agarwood was done by identification of the sesquiterpenes present. Samples were extracted in methylene dichloride at 37.5° C. and nitrogen used to reduce the volume to no less than 0.1 ml. A methylating agent was added before injecting into a Hewlett-Packard 5890 gas chromatograph with a 15 m×0.25 mm DB-1 column. The injector temperature was 280° C. After four minutes the initial column temperature of 50° C. was raised at 10C/min to 340° C. The eluent was detected with a Hewlett-Packard 5972 mass selective detector with the interface at 280° C.

Samples of low, medium and high quality agarwood obtained commercially from Singapore merchants had levels of sesquiterpenes that ranged from 0.3 to 10% of the sample. Sesquiterpenes included, aromadendrene, β-selinene, γ-cadinene, α- and β-guaiene. The levels of sesquiterpenes from samples of agarwood from the experimental trees were at 0% (control wounds) to 1.5% (NaCl treated drill wound treatment after 12 months). Sesquiterpenes included aromadendrene, α-selinene, γ-cadinene, α- and β-guaiene and α-humulene.

Example 7

Multiple, small drill wounds were made at three locations on each tree to observe the effect of wound size and multiple wounds on agarwood formation. Twenty holes approximately 5mm in diameter were drilled approximately 5 cm into the xylem of the tree. Four rows of five wounds were made approximately 2 cm apart. Groups of wounds were made at 30 cm intervals on different sides of the tree. A 10×10 cm area of the bark was cut out around each group of 20 wounds. Trees were harvested after 18 months. The area of discoloration caused by the small drill wounds coalesced together resulting in a large area of discoloration with some agarwood resin formed along the edges. The multiple wounds served to disrupt normal functioning of cells around the wounds and wound closure was delayed. Single small drill wounds made in a tree would not produce significant amounts of agarwood resin since they would close rapidly, but groups of multiple wounds made closely together on the tree disrupted the normal functioning of the xylem and stimulated agarwood production.

Example 8

Fourteen plantation grown trees on Phu Quoc Island were used to test different treatments. Each tree received 8 wounds that were spiraled up the main trunk of the tree separated by approximately 20 cm. A range of different types of wounds and treatments as well as controls were made on each tree. Each treatment was made at a different location on each tree to insure that location of wound did not have an effect. Trees were harvested after 15 months and taken to the laboratory for analyses.

Treatments included:

1. A surface wound approximately 5×5 cm was made by cutting the bark and removing the bark tissue to expose the xylem. No drill hole was made.

3. A ⅝ inch drill wound was made approximately 5 cm into the xylem and a 5×5 cm section of the bark removed around the drill hole and approximately 0.3 g sterile Aquilaria sawdust added to the drill wound.
4. Same as #3 but with approximately 0.3 g of a 1:1 ratio of ferrous chloride and sterile Aquilaria sawdust added to the drill wound.
5. Same as #3 with approximately 0.3 g of a 1:2 ratio of NaCl and sterile Aquilaria sawdust added to the drill wound.
6. Same as #3 but with approximately 0.3 g of a 1:4 ratio of Difco yeast extract and sterile Aquilaria sawdust.
7. Same as #3 but with approximately 0.3 g of a 1:1 ratio of sodium bisulfite and sterile Aquilaria sawdust.
8. Same as #3 but with approximately 0.3 g of a 1:2:4 ratio of Difco nutrient broth: Difco malt extract: sterile Aquilaria sawdust.

After 15 months, 8 trees were harvested and brought to the laboratory for analyses. The area of discoloration and resin formation was determined by splitting the tree through the wounded region and area affected measured using an image analyzer. Area ($cm^2$) was determined for all wounds in the longitudinal plane. Each value is a mean of 8 wounds.

| Wound | Treatment | Area of discoloration/resin |
|---|---|---|
| 1 | Surface wound | 1.4 |
| 2 | Drill wound | 46.3 |
| 3 | Surface wound and drill wound | 27.3 |
| 4 | wounds/ferrous chloride | 112.5 |
| 5 | wounds/NaCl | 48.1 |
| 6 | wounds/yeast extract | 28.6 |
| 7 | wounds/sodium bisulfite | 182.0 |
| 8 | wounds/nutrient media | 34.3 |

This study showed the effectiveness of several treatments for the production of appreciable amounts of agarwood in young Aquilaria trees. Surface wounds do not produce agarwood. Deep penetrating wounds may produce some agarwood as long as the wound site remains open. Compounds that challenge the living cells around the drill wounds in the xylem (e.g. NaCl, sodium bisulfite, ferrous chloride, and any other chemicals that disrupt the normal functioning of living tree cells) increase the area of discoloration within the tree and the amount of agarwood resin formed.

Example 9

Young trees growing at two sites, in home gardens and on agricultural land (Kon Tum, Vietnam and Nui Cam, Vietnam), received 8 wounds per tree. Drill wounds ⅝ inch diameter were drilled approximately 5 cm into the main trunk of each tree in a spiral fashion separated by approximately 20 cm. All drill wounds were scribed to remove a 5×5 cm area of bark around the wound. Fungal treatments consisted of three different types of Basidiomycota obtained from Aquilaria trees in Vietnam. These isolates were not identified to genus but culture morphology indicated they were different genera. Cultures were grown on sterile rice supplemented with malt extract. Cultures were grown for three weeks before inoculation.

Treatments included:
1. Control wound receiving sterile rice
2. Fungal culture 97-14-5
3. Fungal culture 97-13-7
4. Fungal culture 97-11-25
5. Control wound receiving 5 g sterile Aquilaria sawdust
6. Approximately 0.5 g of a 1:4 ratio of sodium bisulfite and sterile Aquilaria sawdust
7. Approximately 0.5 g of a 1:2 ratio of salicylic acid in sterile Aquilaria sawdust
8. Approximately 0.5 g of a 1:4 ratio of ferrous chloride in sterile Aquilaria sawdust After 15 months two trees were harvested from each location and brought to the laboratory for analyses. The mean area for each type of wound was calculated.

| Wound | Treatment | Area of Discoloration $cm^2$ |
|---|---|---|
| Location Kon Tum | | |
| 1 | Control | 22.7 |
| 2 | 97-14-5 | 14.5 |
| 3 | 97-13-7 | 18.0 |
| 4 | 97-11-25 | 17.5 |
| 5 | Control | 11.1 |
| 6 | Sodium bisulfite | 52.3 |
| 7 | Salicylic acid | 16.9 |
| 8 | Ferrous chloride | 18.4 |
| Location Nui Cam | | |
| 1 | Control | 15.5 |
| 2 | 97-14-5 | 18.2 |
| 3 | 97-13-7 | 31.2 |
| 4 | 97-11-25 | 20.9 |
| 5 | Control | 20.6 |
| 6 | Sodium bisulfite | 56.9 |
| 7 | Salicylic acid | 25.5 |
| 8 | Ferrous chloride | 23.3 |

This study indicated that the three different basidiomycetous fungi used did not result in extremely large areas of discoloration and the area was not very different from control wounds. It also indicated that the reduced concentration of sodium bisulfite used in comparison to example 8 caused a reduced amount of discoloration and agarwood resin. Although less area of discoloration was found, agarwood resin did form at the discolored/sound wound interface. When this wood was removed from around the wound and burned it produced a distinctive agarwood aroma. Some compounds such as salicylic acid and ferrous chloride did not produce large areas of discoloration and apparently must be applied in sufficient concentration to affect the living cells in the xylem adjacent to the drill wound. For example, in this experiment ferrous chloride was used in a 1:4 ration with sawdust and moderate amounts of discoloration were observed. In previous experiments it was used in a 1:1 ratio with greater amounts of reaction and agarwood production in the wounded xylem.

Example 10

Iron nails placed into the experimental trees showed a small but significant amount of agarwood when harvested after 6, 15, or 18 months. Reactions observed in the xylem indicate that iron stimulates resin production and iron nails or other sources of iron affect agarwood formation.

Example 11

Figure 4:
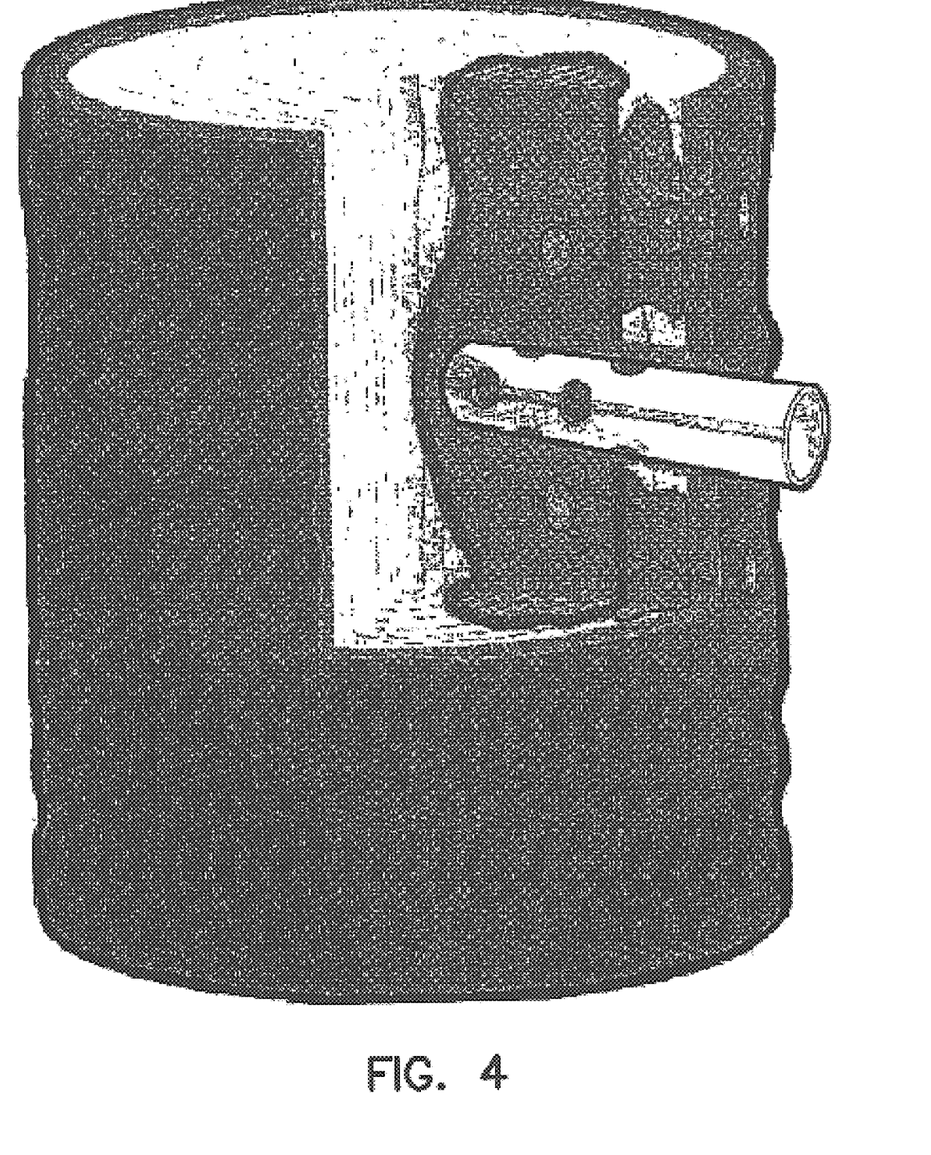
FIG. 4. Schematic drawing showing the effects of new wounds made about 1 year after original wound. These new wounds allow the agarwood to be formed in the new xylem produced after the original wounds are made.

Young trees 5–6 years old growing at two locations, Nui Cam and Kon Turn, Vietnam, were wounded by making ⅝ inch drill wounds into the xylem to a depth of approximately 5.0 cm. Wounds were placed in a spiral up the tree separated by approximately 10 cm. A 5×5 cm area of bark was removed from around the wound and a plastic tube inserted into the wound. The plastic tube had aeration holes drilled into the sides and shallow grooves made into its surface to facilitate air movement along the tube when inserted into the tree (see FIG. 3). The tube extended out from the tree approximately 10 cm so the hole will not close for many years. This tube will insure that the wound will stay open and air will be available to the inner wounded xylem. In addition to wounds receiving only the tubes, other wounds with tubes inserted had a combination of 1:1:3 sodium bisulfite, Difco yeast extract and iron powder added (the iron powder was a 99.6% Fe powder manufactured by J.T. Baker Inc. Phillipsburg, N.J.). Other compounds that cause a localized disruption of the normal functioning of xylem and phloem cells can also be used to prevent internal included phloem from producing secondary cells (that could close the wound from the inside of the drill wound) and to disrupt a greater area of cells in the xylem. As long as the wound remains open to the air, agarwood will progressively accumulate. The greater the disruption of live cells around the wound (without killing the tree) the greater the agarwood production. The tree must remain alive for agarwood to form, as dead trees do not form agarwood. As the tree grew new wood, additional holes were made to allow the zone of agarwood to move into the new xylem (FIG. 4).

Example 12

Trees located in two locations, Nui Cam and Kon Turn, Vietnam, were wounded using a ⅝ inch drill to a depth of approximately 5 cm. Wounds were placed in a spiral fashion on the tree from the ground line up into the crown. Wounds were placed 3 to 5 cm apart. Over time, the wounds were rewounded to keep the wounds open. This was done whenever the wounds appeared to have any wound closure. In these areas of Vietnam they were checked and rewounded every 2–3 months. Trees were wounded with 30 to 70 wounds depending on the size of the tree. These studies show that repeated mechanical wounds that are made deep into the xylem kept the wounds open by preventing external cambial wound closure and internal secondary cell growth by the included phloem. Localized areas of agarwood accumulated immediately adjacent to the wound as long as the wound remained open.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

What is claimed is:

1. A method of producing agarwood comprising
   (a) forming an artificial wound into the xylem in an Aquilaria or Gonystylus tree, and
   (b) providing a means for aerating the wound.
2. The method of claim 1, further comprising repeating steps a and/or b.
3. The method of claim 2, wherein steps a and/or b are repeated after a discolored area has begun forming in the tree.
4. The method of claim 3, wherein the repeated wounding is in the discolored area.
5. The method of claim 1, wherein the wound is formed by cutting, drilling, or chopping or by inserting a nail.
6. The method of claim 1, wherein the wound is formed to reach the xylem.
7. The method of claim 1, wherein the wound is formed to a depth of at least about 1 to 10 cm into the xylem.
8. The method of claim 1, wherein the wound is formed to a depth of about 4–6 cm.
9. The method of claim 1, wherein a series of closely spaced wounds are made in the tree.
10. The method of claim 9, wherein the series of wounds are positioned in a spiral up the tree.
11. The method of claim 9, wherein 30–100 wounds are made.
12. The method of claim 9, wherein the series of wounds are positioned at an interval of about 5 cm apart.
13. The method of claim 1, wherein the aeration means is an aeration device inserted into the wound.
14. The method of claim 13, wherein the aeration device is a nail, tube or pipe inserted into the wound.
15. The method of claim 13, wherein the aeration device comprises aeration holes.
16. The method of claim 13, wherein the aeration device comprises an exterior surface having grooves.
17. The method of claim 13, wherein the aeration device is plastic, bamboo, wood or other organic material, or metal.
18. The method of claim 13, wherein the aeration device is about 2 cm in diameter.
19. The method of claim 13, wherein the aeration device is made of iron.
20. The method of claim 13, wherein the aeration device extends out from the exterior of the tree.
21. The method of claim 20, wherein the aeration device extends out from 2 to 15 cm from the exterior of the free.
22. The method of claim 1, wherein the aeration means is a periodic re-wounding of the wound.
23. The method of claim 22, wherein the aeration means is a monthly re-wounding of the wound.
24. The method of claim 1, wherein the means for aerating the wound comprises scribing a patch of cambium around the wound one or more times over the life span of the tree.
25. The method of claim 1, the method further comprising removing a region of cambium adjoining the wound.
26. The method of claim 1, the method further comprising applying a resin-inducing agent to cells surrounding the wound.
27. The method of claim 26, wherein the agent stimulates resin production.
28. The method of claim 26, wherein the agent kills live parenchyma cells around the wounded region of the xylem.
29. The method of claim 26, wherein the resin-inducing agent is a chemical agent or an organism.
30. The method of claim 26, wherein the organism is a microbe or insect.
31. The method of claim 29, wherein the chemical agent kills cells locally.
32. The method of claim 30, wherein the chemical agent is sodium bisulfite, NaCl, ferric chloride, ferrous chloride, chitin, formic acid, cellobiose, salicyclic acid, iron powder, or yeast extract.
33. The method of claim 29, wherein the chemical agent is 1:1:3 sodium bisulfite, Difco yeast extract and iron powder.
34. The method of claim 26, wherein the microbe is fungus.
35. The method of claim 34, wherein the fungus is *Deuteromyota* sp., *Ascomycota* sp., *Basidiomycota* sp.
36. The method of claim 1, wherein the tree is less than 100 years old.

37. The method of claim 36, wherein the tree is about 2–80 years old.

38. The method of claim 36, wherein the tree is about 3–20 years old.

39. The method of claim 36, wherein the tree is about 3–12 years old.

40. The method of claim 36, wherein the tree is tree not growing naturally in an old growth forest.

41. The method of claim 36, wherein the tree is of the species *Aquilaria malaccensis, A. agallocha, A. baillonii, A. crassna, A. hirta, A. rostrata, A. beccariana, A. cummingiana, A. filaria, A. khasiana, A. microcarpa, A. grandiflora, A. chinesis* or *A. sinensis, A. borneensis,* and *A. bancana*, or *Gonystylus bancanus*.

* * * * *

UNITED STATES PATENT AND TRADEMARK OFFICE
CERTIFICATE OF CORRECTION

PATENT NO. : 6,848,211 B2
DATED : February 1, 2005
INVENTOR(S) : Robert A. Blanchette and Henry Heuveling van Beek

It is certified that error appears in the above-identified patent and that said Letters Patent is hereby corrected as shown below:

Column 13,
Line 61, delete "free" and insert -- tree --.

Column 14,
Line 31, delete "free" and insert -- tree --.
Line 63, insert -- a -- before "fungus".

Signed and Sealed this

Twenty-seventh Day of December, 2005

JON W. DUDAS
*Director of the United States Patent and Trademark Office*